United States Patent
Reykowski et al.

(10) Patent No.: US 11,320,501 B2
(45) Date of Patent: May 3, 2022

(54) CARRIER PHASE TRACKING USING MULTIPLE CARRIERS

(71) Applicant: KONINKLIJKE PHILIPS N.V., Eindhoven (NL)

(72) Inventors: Arne Reykowski, Newberry, FL (US); Paul Franz Redder, Newberry, FL (US); Rodrigo Calderon Rico, Newberry, FL (US)

(73) Assignee: Koninklijke Philips N.V., Eindhoven (NL)

( * ) Notice: Subject to any disclaimer, the term of this patent is extended or adjusted under 35 U.S.C. 154(b) by 78 days.

(21) Appl. No.: 16/969,215

(22) PCT Filed: Jan. 30, 2019

(86) PCT No.: PCT/EP2019/052160
§ 371 (c)(1),
(2) Date: Aug. 12, 2020

(87) PCT Pub. No.: WO2019/158357
PCT Pub. Date: Aug. 22, 2019

(65) Prior Publication Data
US 2020/0408862 A1    Dec. 31, 2020

Related U.S. Application Data

(60) Provisional application No. 62/631,528, filed on Feb. 16, 2018.

(51) Int. Cl.
*G01R 33/36* (2006.01)
*A61B 5/00* (2006.01)
(Continued)

(52) U.S. Cl.
CPC ........ *G01R 33/3692* (2013.01); *A61B 5/0013* (2013.01); *A61B 5/055* (2013.01);
(Continued)

(58) Field of Classification Search
CPC .......... G01R 33/3692; G01R 33/34092; G01R 33/3621; A61B 5/0013; A61B 5/055; H04W 56/0035
See application file for complete search history.

(56) References Cited

U.S. PATENT DOCUMENTS 5,529,068 A    6/1996  Hoenninger et al.
6,044,122 A *  3/2000  Ellersick ............... H04L 7/0338
                                                  327/12
(Continued)

FOREIGN PATENT DOCUMENTS

EP       2594952 A1      5/2013
WO    2015197720 A1     12/2015
(Continued)

OTHER PUBLICATIONS

International Search Report and Written Opinion From PCT/EP2019/052160 dated May 24, 2019.

*Primary Examiner* — Dixomara Vargas (57) ABSTRACT

A clocked electronic device, such as a wireless magnetic resonance (MR) receive coil (20), comprises a wireless receiver or transceiver (30) configured to receive a propagation-delayed wireless clock synchronization signal (54) comprising first and second propagation-delayed carrier signals at respective first and second carrier frequencies separated by a frequency difference, a clock (60) comprising a local oscillator (62) driving a digital counter (64), and at least one electronic signal processing component (66) configured to perform clock synchronization. This includes determining a wrap count (k) from a phase difference ($\varphi_1$) between phases of the first and second propagation-delayed carrier signals, unwrapping a wrapped phase ($\varphi_{2,wrapped}$) of the propagation-delayed wireless clock synchronization sig-
(Continued)

nal using the wrap count to generate an unwrapped phase ($\varphi_{2,wrapped}$), and synchronizing the clock using the unwrapped phase.

22 Claims, 4 Drawing Sheets

(51) Int. Cl.
  *A61B 5/055* (2006.01)
  *G01R 33/34* (2006.01)
  *H04W 56/00* (2009.01)

(52) U.S. Cl.
  CPC ... *G01R 33/34092* (2013.01); *G01R 33/3621* (2013.01); *H04W 56/0035* (2013.01)

(56) References Cited

U.S. PATENT DOCUMENTS

| | | | | |
|---|---|---|---|---|
| 6,058,151 | A | * | 5/2000 | Huang ............... H04L 7/033 375/376 |
| 6,148,052 | A | * | 11/2000 | Bogdan ............. G01R 25/00 327/159 |
| 2005/0084042 | A1 | | 4/2005 | Van Houtum |
| 2007/0061657 | A1 | * | 3/2007 | Chang ............. G01R 31/31858 714/742 |
| 2012/0286787 | A1 | | 11/2012 | Van Liere |
| 2013/0329841 | A1 | * | 12/2013 | Keegan ................ G01S 19/36 375/350 |
| 2015/0066413 | A1 | | 3/2015 | Bhagat et al. |
| 2015/0084644 | A1 | | 3/2015 | Kim et al. |
| 2019/0044774 | A1 | * | 2/2019 | Crols ............... H04W 56/0015 |
| 2019/0045466 | A1 | * | 2/2019 | Shiga ................. G04G 7/02 |
| 2020/0245044 | A1 | | 7/2020 | Menssen ............. E21B 49/00 |
| 2021/0212569 | A1 | * | 7/2021 | Sancho Dur ........ A61B 5/6869 |
| 2021/0341337 | A1 | * | 11/2021 | Chevalier ............ G01J 5/38 |

FOREIGN PATENT DOCUMENTS

| | | |
|---|---|---|
| WO | 2016046696 A2 | 3/2017 |
| WO | 2017103759 A2 | 6/2017 |

* cited by examiner

CARRIER PHASE TRACKING USING MULTIPLE CARRIERS

CROSS REFERENCE TO RELATED APPLICATIONS

This application is a U.S. national phase application of International Application No. PCT/EP2019/052160 filed on Jan. 30, 2019, which claims the benefit of U.S. Provisional Patent Application Ser. No. 62/631,528 filed on Feb. 16, 2018 and is incorporated herein by reference.

FIELD

The following relates generally to the medical imaging arts, wireless component synchronization arts, magnetic resonance imaging arts, positron emission tomography (PET) imaging arts, medical imaging data timestamp synchronization arts, and related arts.

BACKGROUND

In medical imaging, accurate and precise timestamp assignment for acquired imaging data can be of substantial importance. In magnetic resonance (MR) imaging, timestamps are relied upon to temporally correlate acquired imaging data with events of the MR imaging data acquisition sequence such as timing of radio frequency (RF) excitation pulses, applied magnetic field gradients, and so forth. Accurate and precise timestamps are also relied upon to accurately combine phase components of MR signals acquired using a number of MR receive coils, or a receive coil comprising an array of coil elements. More generally, clocks of components such as the MR transmit and receive coils, magnetic field gradient coils, and so forth of an MR imaging system are used to generate and sample various analog signals that are processed to produce an MR image. These clocks should be synchronized with each other to very high accuracy to ensure optimal image quality. For example, in the case of the RF sampling clocks, one digital receiver specification calls for the maximum drift of these clocks to be less than 22 ps. In terms of speed of light, 22 ps is the time it takes for light to travel 7 mm.

Similarly, in time-of-flight positron emission tomography (TOF-PET), accurate time-of-flight information requires that the timestamps of radiation detection events be synchronized to similar precision. In the case of TOF-PET, time of flight spatial localization calls for timestamp accuracies on the order of a few hundred picoseconds or faster.

In the case of MR receive coils with wired RF cable or optical connections, the clock signal propagation delay along the cable is usually invariant respective to positioning of the MR receive coil or external events proximate to the coil. In a wireless MR receive coil, a wireless clock synchronization signal may be employed. Some illustrative examples of this approach are described, for example, in Reykowski et al., Int'l. Publ. No. WO 2017/103759 A2.

In the case of a wireless MR receive coil, the propagation delay of the wireless clock synchronization signal can vary as a function of time due to various factors such as motion of the patient, motion of the patient table, movement of medical professionals in the imaging examination room, or so forth. As previously noted, a spatial movement of as small as 7 mm introduces a change in the propagation delay of 22 ps, which can take the MR imaging system out of specification. A typical solution to this problem is to measure the phase of the wireless clock synchronization signal and to convert the phase to a time delay on the basis of the relationship $\Delta\varphi = 2\pi f \cdot \Delta t$ where $\Delta t$ is the (change in) propagation delay to be estimated, $\Delta\varphi$ is the measured phase shift relative to some reference phase, and $f$ is the carrier frequency of the wireless clock synchronization signal. The phase $\varphi(t)$ can be monitored as a function of time relative to a reference phase $\varphi(t_0)=0$ at a designated reference time $t_0$, and the propagation delay $\Delta t$ at a time $t$ is given by $$\Delta t = \frac{\varphi(t) - \varphi(t_0)}{2\pi f}.$$

However, a problem can arise in that the measured phase $\varphi(t)$ is the wrapped phase. If $\Delta t$ is sufficiently large, then the actual carrier phase might exceed the range of $\pm 180°$ and phase wrap occurs. The direct measurement is of the wrapped phase $\varphi^{wrapped}(t)$, which is limited to the range $[-180°, +180°]$. On the other hand, to compute $\Delta t$ without ambiguity, the unwrapped phase $\varphi^{unwrapped}(t) = \varphi^{wrapped}(t) + 2\pi k$ is needed, where $k$ is an integer value.

If the phase increments between subsequent measurements of $\varphi^{wrapped}(t)$ are small enough, then the true (i.e. unwrapped) carrier phase $\varphi^{unwrapped}(t)$ can be obtained by accumulating the phase increments between the measured values of $\varphi^{wrapped}(t)$. However, this method requires continuous monitoring of the measured (wrapped) carrier phase $\varphi^{wrapped}(t)$, which may not always be possible. For example, if there is a brief loss of communication, it will not be known with certainty whether phase wrap occurred during the communication lapse.

The following discloses certain improvements.

SUMMARY

In some embodiments disclosed herein, a clocked electronic device includes a wireless receiver or transceiver configured to receive a propagation-delayed wireless clock synchronization signal. That signal comprises first and second propagation-delayed carrier signals at respective first and second carrier frequencies separated by a frequency difference. The clocked electronic device further includes a clock, for example comprising a local oscillator (LO) driving a digital counter, and still further includes an electronic signal processing component configured to perform clock synchronization. The clock synchronization includes: determining a wrap count (k) from a phase difference ($\varphi_1$) between phases of the first and second propagation-delayed carrier signals; unwrapping a wrapped phase ($\varphi_{2,wrapped}$) of the propagation-delayed wireless clock synchronization signal using the wrap count to generate an unwrapped phase ($\varphi_{2,unwrapped}$); and synchronizing the clock using the unwrapped phase. The wrapped phase ($\varphi_{2,wrapped}$) of the propagation-delayed wireless clock synchronization signal may, for example, be the wrapped phase of one of: the first propagation-delayed carrier signal; the second propagation-delayed carrier signal; a combined signal that combines the first and second propagation-delayed carrier signals; and a third propagation-delayed carrier signal of the propagation-delayed wireless clock synchronization signal wherein the third propagation-delayed carrier signal is different from the first propagation-delayed carrier signal and is different from the second propagation-delayed carrier signal. In one illustrative approach, the clock synchronization further includes determining a propagation delay ($\Delta t$) of the propagation-delayed wireless clock synchronization signal from the unwrapped phase ($\varphi_{2,unwrapped}$) and synchronizing the clock using the determined propagation delay.

In some embodiments, the aforementioned clocked electronic device comprises a wireless medical imaging device component configured to collect samples of physiological or medical imaging data, and the electronic signal processing component is further configured to assign timestamps to the samples. The timestamps are obtained from the clock synchronized using the unwrapped phase. The wireless medical imaging device component may, for example, comprise a wireless magnetic resonance (MR) receive coil configured for use with an MR imaging device. In another embodiment, the wireless medical imaging device component may, for example, comprise an electrocardiograph (ECG) or other physiological sensing device configured for use with an MR imaging device. As yet another illustrative non-limiting example, the wireless medical imaging device component may, for example, comprise a radiation detector module of a positron emission tomography (PET) imaging device.

In another disclosed aspect, the aforementioned clocked electronic device may further include (or be wirelessly operatively coupled with) a wireless clock synchronization signal generator that includes a radio frequency (RF) signal generator configured to generate a clock synchronization signal, and a transmitter or transceiver connected to wirelessly transmit the clock synchronization signal into free space as a wireless clock synchronization signal. The propagation-delayed wireless clock synchronization signal thus comprises the wireless clock synchronization signal transmitted through free space to the wireless receiver or transceiver. In some non-limiting illustrative embodiments, the RF signal generator may comprise a dual sideband (DSB) modulator configured to modulate a master carrier signal with a baseband signal at a baseband frequency equal to one-half of the frequency difference between the first and second carrier frequencies.

In some embodiments, the wireless receiver or transceiver, the clock, and the electronic signal processing component comprise a wireless device, and the wireless clock synchronization signal generator is not part of the wireless device.

In another disclosed aspect, a clock synchronization method is disclosed. Using a wireless receiver or transceiver, a free space transmission is received of a propagation-delayed wireless clock synchronization signal comprising first and second propagation-delayed carrier signals at respective first and second carrier frequencies separated by a frequency difference. Using an electronic signal processing component, operations are performed including: determining a wrap count (k) from a phase difference ($\varphi_1$) between phases of the first and second propagation-delayed carrier signals; unwrapping a wrapped phase ($\varphi_{2,wrapped}$) of the propagation-delayed wireless clock synchronization signal using the wrap count to generate an unwrapped phase ($\varphi_{2,unwrapped}$); and synchronizing an electronic clock using the unwrapped phase. The clock synchronization method may further include operating a radio frequency (RF) signal generator to generate a clock synchronization signal and wirelessly transmitting the clock synchronization signal into free space as a wireless clock synchronization signal. The propagation-delayed wireless clock synchronization signal then comprises the wireless clock synchronization signal transmitted through free space to the wireless receiver or transceiver. In some such embodiments, the wireless clock synchronization signal generator comprises a dual sideband (DSB) modulator configured to modulate a master carrier signal with a baseband signal at a baseband frequency equal to one-half of the frequency difference between the first and second carrier frequencies.

One advantage resides in providing clock synchronization using a wireless clock synchronization signal in which ambiguities due to possible phase wrapping are accounted for.

Another advantage resides in providing a wireless MR coil or other wireless MR component or other wireless medical imaging component providing such clock synchronization in which ambiguities due to possible phase wrapping are accounted for.

Another advantage resides in providing a wireless MR coil or other wireless medical imaging component with improved timestamp reliability by accounting for possible phase wrapping during synchronization with a wireless clock synchronization signal.

Another advantage resides in providing one or more of the foregoing benefits using a wireless clock synchronization signal with relatively narrow bandwidth.

Another advantage resides in providing one or more of the foregoing benefits using a wireless clock synchronization signal generated using inexpensive circuitry such as a dual sideband (DSB) modulator circuit.

Another advantage resides in providing one or more of the foregoing benefits in which clock synchronization is robust against brief interruptions in the communication of the wireless clock synchronization signal.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
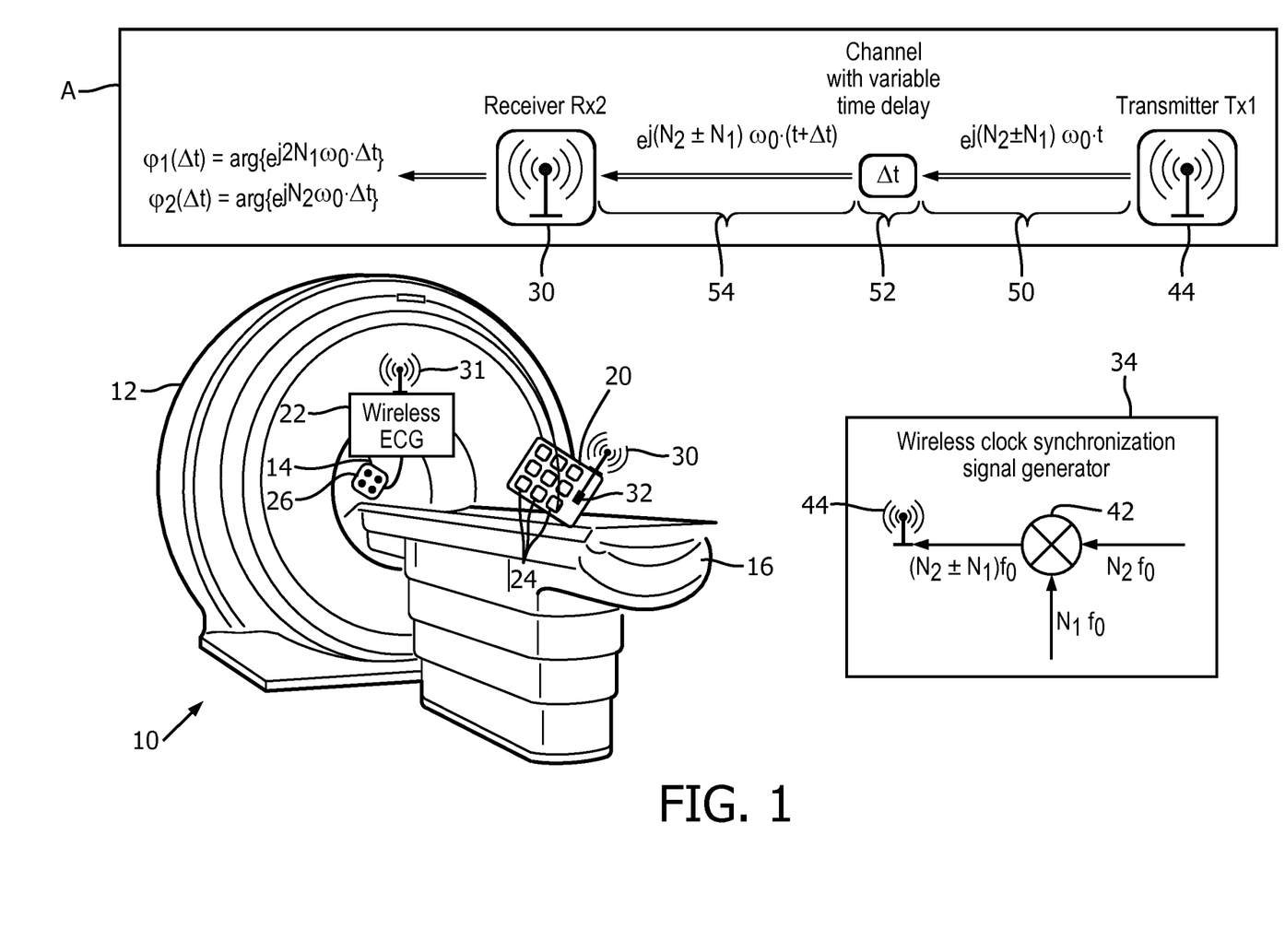
FIG. 1 diagrammatically illustrates a magnetic resonance (MR) imaging device including wireless components having clocks synchronized with a wireless clock synchronization signal. The upper inset diagrammatically shows determination of the wrapped phase $\varphi_2$ and the phase difference $\varphi_1$ used to unwrap the phase.

With reference to FIG. 1, an illustrative medical imaging device 10 comprises a magnetic resonance (MR) imaging scanner, which in the illustrative example includes a housing or gantry 12 containing various components which are not shown in FIG. 1, such as by way of non-limiting illustrative example a superconducting or resistive magnet generating a static ($B_0$) magnetic field, magnetic field gradient coils for superimposing magnetic field gradients on the $B_0$ magnetic field, a whole-body radio frequency (RF) coil for applying RF pulses to excite and/or spatially encode magnetic resonance in an imaging subject disposed in an MR bore 14 or other MR examination region, and/or so forth. A robotic patient couch 16 or other subject support enables loading a medical patient, a subject undergoing a medical screening, or other imaging subject into the MR bore 14 for imaging.

As will be appreciated by medical personnel, usage of medical imaging devices such as the illustrative MR imaging scanner 10 can entail the positioning and operation of numerous medical imaging device components. By way of non-limiting illustration, FIG. 1 shows two such medical imaging device components that may be of use: a wireless MR receive coil 20 configured for use with the MR imaging device 10, and an electrocardiograph (ECG) 22 configured for use with the MR imaging device 10. The wireless MR receive coil 20 is configured for use with the MR imaging device 10 at least insofar as it includes at least one coil element 24 (illustrative array of nine coil elements 24) configured by tuning to the MR frequency and optionally by other aspects such as inclusion of a preamplifier to amplify the MR signal, physical shaping to be positioned next to an anatomical region undergoing imaging, and/or so forth, to receive an MR signal generated by operation of the MR imaging device 10. The illustrative ECG 22 is configured for use with the MR imaging device 10 by employing a compact electrode pad 26 with a reduced number of electrodes arranged in an EASI configuration or the like to facilitate acquisition of ECG physiological data in the close confines of the MR bore 14, and may be further configured for use with the MR imaging device 10 by aspects such as limited or eliminated use of ferromagnetic-core inductors in the electronics, extensive RF shielding to mitigate RF interference, and/or so forth.

The illustrative medical imaging device 10 and the illustrative clocked electronic devices 20, 22 are merely illustrative examples, and it is contemplated to employ clocked electronic devices including clock synchronization as disclosed herein for a wide range of devices for a wide range of applications. The disclosed clock synchronization is particularly useful in the context of clocked wireless electronic devices, but may be used in conjunction with other types of clocked electronic devices. For example, a time-of-flight positron emission tomography (TOF-PET) imaging device employs one or more rings of radiation detector modules for detecting 511 keV gamma radiation emitted by positron-electron annihilation events. Each positron-electron annihilation event emits two 511 keV gamma rays, which are emitted in opposite directions to satisfy conservation of momentum. Two such 511 keV gamma rays detected within a narrow time window is identified as a coincident 511 keV gamma ray pair; when TOF localization is employed, the time difference (if any) between these two coincident detections is converted to spatial localization along the line of response (LOR) connecting the detections. As the gamma rays travel at the speed of light, TOF localization requires precision synchronization of all radiation detector modules of the PET scanner to an accuracy of a few tens or hundreds of picoseconds or better. Although the radiation detector modules (which are medical imaging device components) may be wired to port off medical imaging data (here digitized or analog signals indicating timestamped gamma ray detection events), it is nonetheless contemplated to employ a clock synchronization method as disclosed herein employing broadcast of a wireless clock synchronization signal to the radiation detector modules in order to substantially reduce the wiring needed for installing the radiation detector modules. Beyond this, it is still further contemplated to employ the disclosed clock synchronization in applications beyond medical imaging, as the disclosed clock synchronization using a wireless clock synchronization signal comprising first and second propagation-delayed carrier signals at respective first and second carrier frequencies separated by a frequency difference may be usefully employed in any context in which ambiguity in synchronization due to phase wrapping of the wireless clock synchronization signal is a concern.

In the following, the illustrative description focuses on the illustrative wireless MR receive coil 20, which as diagrammatically shown includes a wireless receiver or transceiver 30 configured to receive a propagation-delayed wireless clock synchronization signal comprising first and second propagation-delayed carrier signals at respective first and second carrier frequencies separated by a frequency difference, and electronics 32 including at least an on-board clock and at least one electronic signal processing component configured to generate timestamped samples of the MR signal received by the at least one coil element 24 using the on board clock and further configured to perform clock synchronization as disclosed herein. Furthermore, a wireless clock synchronization signal generator 40 includes an RF signal generator 42 configured to generate a clock synchronization signal, and a transmitter or transceiver 44 connected to wirelessly transmit the clock synchronization signal into free space as a wireless clock synchronization signal. The aforementioned propagation-delayed wireless clock synchronization signal thus comprises the wireless clock synchronization signal transmitted from the transmitter or transceiver 44 through free space to the wireless receiver or transceiver 30 of the wireless MR receive coil 20 (i.e. illustrative clocked electronic device).

While the clock synchronization is described with reference to the illustrative wireless MR receive coil 20, it will be appreciated that any other clocked electronic device may be similarly constructed to employ the disclosed clock synchronization utilizing the wireless clock synchronization signal output by the transmitter or transceiver 44 of the wireless clock synchronization signal generator 40. In this way, all such clocked electronic devices will be synchronized to the same wireless clock synchronization signal and hence will be synchronized with each other. By way of further illustration, the wireless ECG 22 includes a wireless receiver or transceiver 31 analogous to the wireless receiver or transceiver 30 of the wireless MR receive coil 20, along with electronics (not shown for the ECG 22) comprising an on-board clock and at least one electronic signal processing component configured to generate timestamped samples of (in this case) ECG signals received via the electrodes pad 26 using the on board clock and further configured to perform clock synchronization analogously to the approach described for the MR coil 20 as illustrative example.

With continuing reference to FIG. 1 and with particular reference to the diagrammatically drawn embodiment of the wireless clock synchronization signal generator 34 and the diagrammatic upper Inset A, the clock synchronization including phase unwrapping is described. In the illustrative wireless clock synchronization signal generator 34, the RF signal generator comprises a dual sideband (DSB) modulator 42 configured to modulate a master carrier signal, at a frequency denoted $N_2 f_0$, with a baseband signal at a baseband frequency denoted $N_1 f_0$ which is equal to one-half of the frequency difference between the first and second carrier frequencies. The DSB modulation produces two signals: an upper sideband signal at frequency $(N_2+N_1)f_0$, and a lower sideband signal at frequency $(N_2-N_1)f_0$. The generated clock synchronization signal includes both the upper and lower sideband components, and is denoted herein by the shorthand notation $(N_2 \pm N_1)f_0$. Turning now to the upper Inset A, the transmitter or transceiver 44 of the wireless clock synchronization signal generator 40 outputs this generated clock synchronization signal as a wireless clock synchronization signal 50 into free space. (Note that Inset A employs angular frequencies denoted by ω which relate to corresponding frequencies f in Hertz by the well-known relationship ω=2πf). The transmission through free space can be viewed as a transmission channel 52 as diagrammatically shown in Inset A. The propagation-delayed wireless clock synchronization signal 54 received at the wireless receiver or transceiver 30 of the wireless MR receive coil 20 is thus the wireless clock synchronization signal 50 transmitted through free space 52 to the wireless receiver or transceiver 30.

With continuing reference to FIG. 1, Inset A, the free space channel 52 introduces a delay Δt. This delay can, in general, vary as a function of time due to movements of the MR receive coil 20, interposition of a moving radiologist or other physical entity passing through and distorting the free space channel 52, or so forth. Moreover, it will be appreciated that the free space channel delay Δt will differ for different clocked electronic devices which are to be synchronized together using the wireless clock synchronization signal 50—for example, the free space channel delay Δt may be different for the MR receive coil 20 and the ECG 22, and both may in general vary as a function of time. Typically, at a synchronization reference time $t_0$ the phase of the wireless clock synchronization signal at each synchronized clocked electronic device is set to zero (that is, the reference phase is set as $\varphi_0(t_0)=0$ for each device), and thereafter the variable time delay at a time t is determined from the relationship $\Delta\varphi=(\varphi(t)-\varphi(t_0))=2\pi f\cdot(\Delta t(t)-\Delta t(t_0))$. With $\varphi_0(t_0)=0$ and $\Delta t(t_0)=0$ being set for the reference time $t_0$, this reduces to $\Delta\varphi(t)=2\pi f\cdot\Delta t(t)$ which is sometimes written herein using the shorthand $\Delta\varphi=2\pi f\cdot\Delta t$ with the understanding that $\Delta\varphi$ and $\Delta t$ are for a certain understood time t (such as the current time). The phase shift Δφ or, equivalently, the time delay Δt, at time t can then be used to adjust for the variable time delay in synchronizing the on-board clock of the clocked electronic device. However, as previously discussed herein, this approach has a flaw—if the phase shift Δφ becomes wrapped, because Δφ becomes larger than 180° (or +π using angular units) or smaller than −180° (or −π using angular units), then there is an ambiguity and the time shift computed as $$\Delta t = \frac{\Delta\varphi}{2\pi f}$$

(using angular units for Δφ) is in error since it is the wrapped angular phase shift $\Delta\varphi^{wrapped}$ that is measured; whereas, it is the unwrapped angular phase shift $\Delta\varphi^{unwrapped}$ that is needed to unambiguously compute the variable time delay according to $$\Delta t = \frac{\Delta\varphi^{unwrapped}}{2\pi f}.$$

This ambiguity is overcome as disclosed herein by the use of the propagation-delayed wireless clock synchronization signal comprising first and second propagation-delayed carrier signals at respective first and second carrier frequencies separated by a frequency difference. In the illustrative examples, the notation of the DSB modulation example is used, so that the propagation-delayed wireless clock synchronization signal 54 comprises a first (here upper sideband) propagation-delayed carrier signal at angular frequency $(N_2+N_1)\omega_0$ and a second (here lower sideband) propagation-delayed carrier signal at angular frequency $(N_2-N_1)\omega_0$. These two carrier frequencies are separated by the frequency difference $2N_1\omega_0$. If the baseband frequency $N_1f_0$ is set to a relatively small value, e.g. 50 MHz or lower, then the frequency difference $2N_1f_0$ between the upper and lower sidebands will be twice this baseband frequency, e.g. 100 MHz or lower in this quantitative example. The phase difference between the two propagation delayed carrier signals is denoted herein as $\varphi_1$. This phase difference can be related to the propagation delay Δt of the propagation-delayed wireless clock synchronization signal 54 as follows. The phase shift of the upper sideband is $(N_2+N_1)\omega_0\cdot\Delta t$. The phase shift of the lower sideband is $(N_2-N_1)\omega_0\cdot\Delta t$. The phase difference is then:

$$\varphi_1=[(N_2+N_1)\omega_0\cdot\Delta t]-[(N_2-N_1)\omega_0\cdot\Delta t]=2N_1\omega_0\cdot\Delta t \quad (1)$$

This phase shift $\varphi_1$ is for a difference signal with an "effective" frequency equal to the frequency difference $2N_1f_0$ separating the two carrier frequencies (e.g., separating the upper and lower sidebands in the DSB modulation example). The low frequency corresponds to a long propagation delay Δt needed to wrap the phase shift $\varphi_1$. For example, if $N_1f_0$=50 MHz then then the phase shift $\varphi_1$ wraps only for a propagation delay longer than $$\Delta t = \frac{\Delta\varphi_1 = \pi}{2\pi(N_1f_0)} = \frac{\pi}{2\pi(50\text{ MHz})} = 0.01\ \mu s = 10000\text{ ps.}$$

Accordingly, wrapping of the phase difference $\varphi_1$ between the two carriers separated by 100 MHz or less in frequency is not expected for realistic changes in position of the MR receive coil 20 or for other events such as the radiologist or other entity interposing into the free space transmission channel 52.

The phase difference $\varphi_1$ between the two propagation delayed carrier signals has a relatively low "effective" frequency corresponding to the frequency difference $2N_1f_0$. While this is advantageous to avoid phase wrapping of the phase difference $\varphi_1$, it also means that the phase difference $\varphi_1$ between the two propagation delayed carrier signals generally has insufficient temporal resolution to provide the desired time synchronization precision on the order of tens or hundreds of picoseconds. Accordingly, in embodiments disclosed herein, a wrap count, denoted herein as k, is determined from a phase difference $\varphi_1$ between phases of the first and second propagation-delayed carrier signals. This wrap count measures the wrapping (which could be zero) of a wrapped phase ($\varphi_{2,wrapped}$) of the propagation-delayed wireless clock synchronization signal 54. Thus, the wrap count k is used to unwrap the wrapped phase $\varphi_{2,wrapped}$ of the propagation-delayed wireless clock synchronization signal 54 in order to generate an unwrapped phase ($\varphi_{2,unwrapped}$). This unwrapped phase is of sufficient temporal precision to provide for synchronizing the on-board clock of the clocked electronic device (e.g. MR receive coil 20) with the desired high temporal resolution, e.g. on the order of a few picoseconds to a few tens of picoseconds in some embodiments.

The wrapped phase $\varphi_{2,wrapped}$ of the propagation-delayed wireless clock synchronization signal 54 that is unwrapped and then used for the clock synchronization may be variously obtained. In the illustrative example in which the wireless clock synchronization signal 50 is generated by DSB modulation, the propagation-delayed wireless clock synchronization signal 54 includes two components: the upper sideband at frequency $(N_2+N_1)f_0$, and the lower sideband at frequency $(N_2-N_1)f_0$. Thus, the wrapped phase $\varphi_{2,wrapped}$ may be the phase of the upper sideband extracted using an analog or digital phase detector. Alternatively, the wrapped phase $\varphi_{2,wrapped}$ may be the phase of the lower sideband extracted using an analog or digital phase detector. In another contemplated approach, the wrapped phase $\varphi_{2,wrapped}$ may be the phase of a combined signal that combines the first and second propagation-delayed carrier signals, e.g. a combined signal at the master carrier frequency $N_2f_0$ produced by mixing the propagation-delayed wireless clock synchronization signal 54 with a local oscillator signal followed by filtering. As yet another contemplated approach, the wrapped phase $\varphi_{2,wrapped}$ may be the phase of a third propagation-delayed carrier signal (not illustrated) of the propagation-delayed wireless clock synchronization signal, where the third propagation-delayed carrier signal is different from the first propagation-delayed carrier signal and is different from the second propagation-delayed carrier signal. For example, the DSB modulation performed by the illustrative wireless clock synchronization signal generator 34 performs DSB-SC (i.e. "suppressed carrier") modulation since the output $(N_2 \pm N_1)f_0$ of the mixer 42 does not include any component at the master carrier frequency $N_2f_0$. In an alternative DSB-RC ("reduced carrier") modulation approach a component at the master carrier frequency $N_2f_0$ is added to the output (e.g., using a signal adder, not shown) to serve as a reference—in this case the wrapped phase $\varphi_{2,wrapped}$ may be the phase of that reference carrier at master carrier frequency $N_2f_0$.

In the interest of mathematical simplicity, in the following it is assumed the phase $\varphi_2$ is the phase of a third propagation-delayed carrier signal at the master carrier frequency $N_2f_0$. It will be appreciated that if instead the phase of the upper sideband at frequency $(N_2+N_1)f_0$ is used; or alternatively if instead the phase of the lower sideband at frequency $(N_2-N_1)f_0$ is used, this has no practical impact on the result if $N_2 \gg N_1$, that is, if the master carrier frequency $N_2f_0$ is much greater than the baseband frequency $N_1f_0$. This is expected to typically be the case, e.g. in some illustrative embodiments $(N_2+N_1)f_0 > 1$ GHz while the frequency difference $2N_1 \leq 100$ MHz. In this illustrative example where the phase $\varphi_2$ is the phase of a third propagation-delayed carrier signal at the master carrier frequency $N_2f_0$, it follows that the unwrapped phase is given by (all phases in the following are angular phases, i.e. measured in radians):

$$\varphi_{2,unwrapped} = N_2 \omega_0 \cdot \Delta t \quad (2)$$

This result changes trivially if a different component or combined signal of the propagation-delayed wireless clock synchronization signal 54 is chosen, e.g. if the phase $\varphi_2$ is chosen as the phase of the upper sideband component then this becomes:

$$\varphi_{2,unwrapped} = (N_2+N_1)\omega_0 \cdot \Delta t \quad (2a)$$

while if the phase $\varphi_2$ is chosen as the phase of the lower sideband component then this becomes:

$$\varphi_{2,unwrapped} = (N_2-N_1)\omega_0 \cdot \Delta t \quad (2b)$$

For the expected case where $N_2 \gg N_1$, the dispersion of the free space channel 52 should be negligible, and in this case the propagation delay $\Delta t$ should be the same (within negligible error) for each of the lower sideband $(N_2-N_1)f_0$, upper sideband $(N_2+N_1)f_0$, and (optional) master carrier $N_2f_0$ frequencies of the free space channel 52 over which the wireless clock synchronization signal 50 is transmitted.

For a given $\Delta t$ there is a linear relationship between $\varphi_1$ of Equation (1) and the unwrapped phase $\varphi_{2,unwrapped}$ of Equation (2), given by:

$$\varphi_1 = \frac{2N_1}{N_2} \varphi_{2,unwrapped} \quad (3)$$

In principle, Equation (3) could be inverted to yield $\varphi_{2,unwrapped}$ from the measured phase difference $\varphi_1$ (which is assumed to be not wrapped due to its low effective frequency). However, as previously discussed this would result in an estimate for $\varphi_{2,unwrapped}$ which would not provide the desired temporal resolution on the order of picoseconds to tens of picoseconds. Instead, as disclosed herein the phase difference $\varphi_1$ is used to determine a wrap count k which quantifies how many times (possibly zero) that the measured phase $\varphi_{2,wrapped}$ is wrapped:

$$\varphi_{2,unwrapped} = \varphi_{2,wrapped} + 2\pi k \quad (4)$$

where k is the wrap count and is an integer indicating the count (possibly zero) of the number of times the wrapped phase $\varphi_{2,wrapped}$ is wrapped. The wrapped phase $\varphi_{2,wrapped}$ of the propagation-delayed wireless clock synchronization signal is then unwrapped using the wrap count k to generate the unwrapped phase $\varphi_{2,unwrapped}$. To this end, Equation (3) can be recast using Equation (4) as follows:

$$\varphi_1 = \frac{2N_1}{N_2} \varphi_{2,unwrapped} = \frac{2N_1}{N_2}(\varphi_{2,wrapped} + 2\pi k) \quad (5)$$

Solving Equation (5) for the wrap count k yields:

$$k \approx \left[\frac{\varphi_1}{2N_1} - \frac{\varphi_{2,wrapped}}{N_2}\right] \cdot \frac{N_2}{2\pi} \quad (6)$$

However, this is not precisely correct, because the wrap count k must be an integer. In view of measurement error and considering that the measured phase difference $\varphi_1$ is a coarse value compared with the measured phase $\varphi_{2,wrapped}$, the result of Equation (6) is unlikely to be precisely an integer. Incorporating knowledge that the wrap count k must be an integer yields:

$$k = \text{round}\left\{\left[\frac{\varphi_1}{2N_1} - \frac{\varphi_{2,wrapped}}{N_2}\right] \cdot \frac{N_2}{2\pi}\right\} \quad (7)$$

Combining Equations (4) and (7) yields the desired unwrapped phase $\varphi_{2,unwrapped}$ at the desired high temporal resolution of the measured wrapped phase $\varphi_{2,wrapped}$ according to:

$$\varphi_{2,unwrapped} = \varphi_{2,wrapped} + 2\pi \cdot \text{round}\left\{\left[\frac{\varphi_1}{2N_1} - \frac{\varphi_{2,wrapped}}{N_2}\right] \cdot \frac{N_2}{2\pi}\right\} \quad (8)$$

If, instead, the measured wrapped phase $\varphi_{2,wrapped}$ is chosen as the wrapped phase of the upper sideband at frequency $(N_2+N_1)f_0$, then in Equation (8) each occurrence of $N_2$ is replaced by $(N_2+N_1)$ yielding:

$$\varphi_{2,unwrapped} = \varphi_{2,wrapped} + 2\pi \cdot \text{round}\left\{\left[\frac{\varphi_1}{2N_1} - \frac{\varphi_{2,wrapped}}{N_2+N_1}\right] \cdot \frac{N_2+N_1}{2\pi}\right\} \quad (8a)$$

Likewise, if the measured wrapped phase $\varphi_{2,wrapped}$ is chosen as the wrapped phase of the lower sideband at frequency $(N_2-N_1)f_0$, then in Equation (8) each occurrence of $N_2$ is replaced by $(N_2-N_1)$ yielding:

$$\varphi_{2,unwrapped} = \varphi_{2,wrapped} + 2\pi \cdot \text{round}\left\{\left[\frac{\varphi_1}{2N_1} - \frac{\varphi_{2,wrapped}}{N_2-N_1}\right] \cdot \frac{N_2-N_1}{2\pi}\right\} \quad (8b)$$

Figure 2:
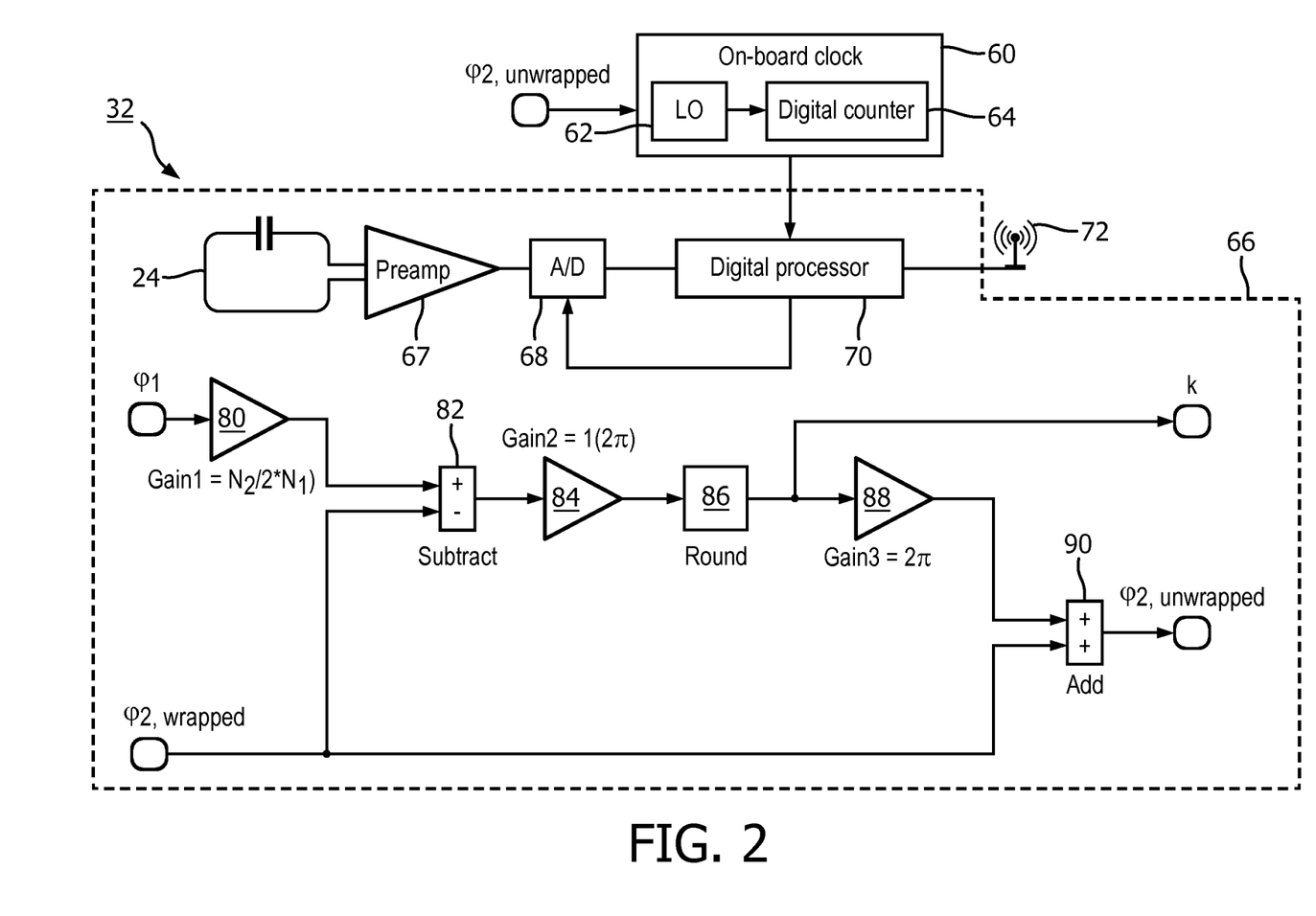
FIG. 2 diagrammatically illustrates a process for unwrapping the wrapped phase $\varphi_2$ using the phase difference $\varphi_1$.

With reference now to FIG. 2, an illustrative example of the electronics 32 of the MR receive coil 20 of FIG. 1 is described. The electronics 32 include an on-board clock 60 for assigning timestamps to MR signal samples. The illustrative clock 60 includes a local oscillator (LO) 62 that drives a digital counter 64. The electronics 32 further include at least one electronic signal processing component 66 configured to perform clock synchronization and, in the illustrative MR receive coil example, to process the received MR signal. Toward the latter end, the at least one electronic signal processing component 66 includes a preamplifier 67 that amplifies the MR signal received by the at least one coil loop 24 and an analog-to-digital (A/D) converter 68 to generate digital samples of the received and amplified MR signal. While FIG. 2 illustrates a single preamplifier-A/D converter chain 67, 68, there may be parallel chains to accommodate multiple receive channels, e.g. the MR receive coil 20 of FIG. 1 includes nine coil loops 24 which may feed nine separate channels, or may be variously combined to feed fewer than nine channels.

The at least one electronic signal processing component 66 further includes a digital processor 70 (e.g. a digital microprocessor, digital microcontroller, field-programmable gate array (FPGA), and/or so forth) configured to generate timestamped samples of the MR signal received by the at least one coil element 24 (and amplified and digitized by the signal processing chain 67, 68) using the on-board clock 60. In one approach, an MR signal sample acquisition is triggered by an increment of the digital counter 64 of the clock 60 (or by occurrence of some set number of increments, e.g. every 16 counts). This triggers latching of the A/D converter 68 to lock in a sample at the time of the increment of the digital counter 64. The digital MR signal sample is then read from the latched A/D converter 68 into the digital processor 70 and is assigned a timestamp read into the digital processor 70 from the digital counter 64. This is merely one illustrative approach for generating the timestamped MR signal samples. The acquired samples may be wirelessly output by a transmitter or transceiver 72, which may in some embodiments be a transceiver 72 that is the same as the transceiver 30 (see FIG. 1) that receives the propagation-delayed wireless clock synchronization signal 54, although different receiver/transmitter/transceiver units are also contemplated. Instead of porting the MR signal samples off the MR receive coil wirelessly, other approaches are contemplated such as using a fiber optic connection or an electrical cable.

With continuing reference to FIG. 2, the at least one electronic signal processing component 66 is further configured to perform clock synchronization to synchronize the clock 60 using the wireless clock synchronization signal 50 (see FIG. 1). The illustrative clock synchronization components include an amplifier 80 with gain $$\frac{N_2}{2N_1},$$

a subtractor 82, an amplifier 84 with gain $$\frac{1}{2\pi},$$

a round functional component 86, an amplifier 88 with gain $2\pi$, and an adder 90 interconnected as shown in FIG. 2 to implement Equation (8). The various components 80, 82, 84, 86, 88, 90 may be implemented as analog components or as digital signal processing (DSP), e.g. implemented by suitable programming of the digital processor 70 or of a separate digital processor (not shown). The clock synchronization components 80, 82, 84, 86, 88, 90 receive as input the phase difference $\varphi_1$ and the wrapped phase $\varphi_{2,wrapped}$. These values $\varphi_1$ and $\varphi_{2,wrapped}$ may be obtained by an analog or digital phase detector along with frequency filters to isolate the upper and lower sideband signals of the propagation-delayed wireless clock synchronization signal 54 (components not shown). For example, in one embodiment the propagation-delayed wireless clock synchronization signal 54 is digitized by an A/D converter and the digitized propagation-delayed wireless clock synchronization signal waveform is fed into the electronic processor 70 to perform the phase detection. The output of the illustrative clock synchronization components 80, 82, 84, 86, 88, 90 is the unwrapped phase $\varphi_{2,unwrapped}$ and the wrap count k—however, the latter output is not used and can optionally be omitted. In the illustrative example, the unwrapped phase $\varphi_{2,unwrapped}$ is input to the clock 60 for synchronization; alternatively, additional clock synchronization component(s) may be added to extract the propagation delay $\Delta t$ in accordance with:

$$\Delta t = \frac{\varphi_{2,unwrapped}}{2\pi f} \quad (9)$$

where f is the frequency of the component of the propagation-delayed wireless clock synchronization signal 54 selected for determining $\varphi_{2,unwrapped}$; e.g., $f=(N_2+N_1)f_0$ for the upper sideband component, or $f=(N_2-N_1)f_0$ for the lower sideband component, or $f=N_2f_0$ for a component at the master carrier frequency, et cetera. In these alternative embodiments, the propagation delay $\Delta t$ is input to the clock 60 for synchronization.

Figure 3:
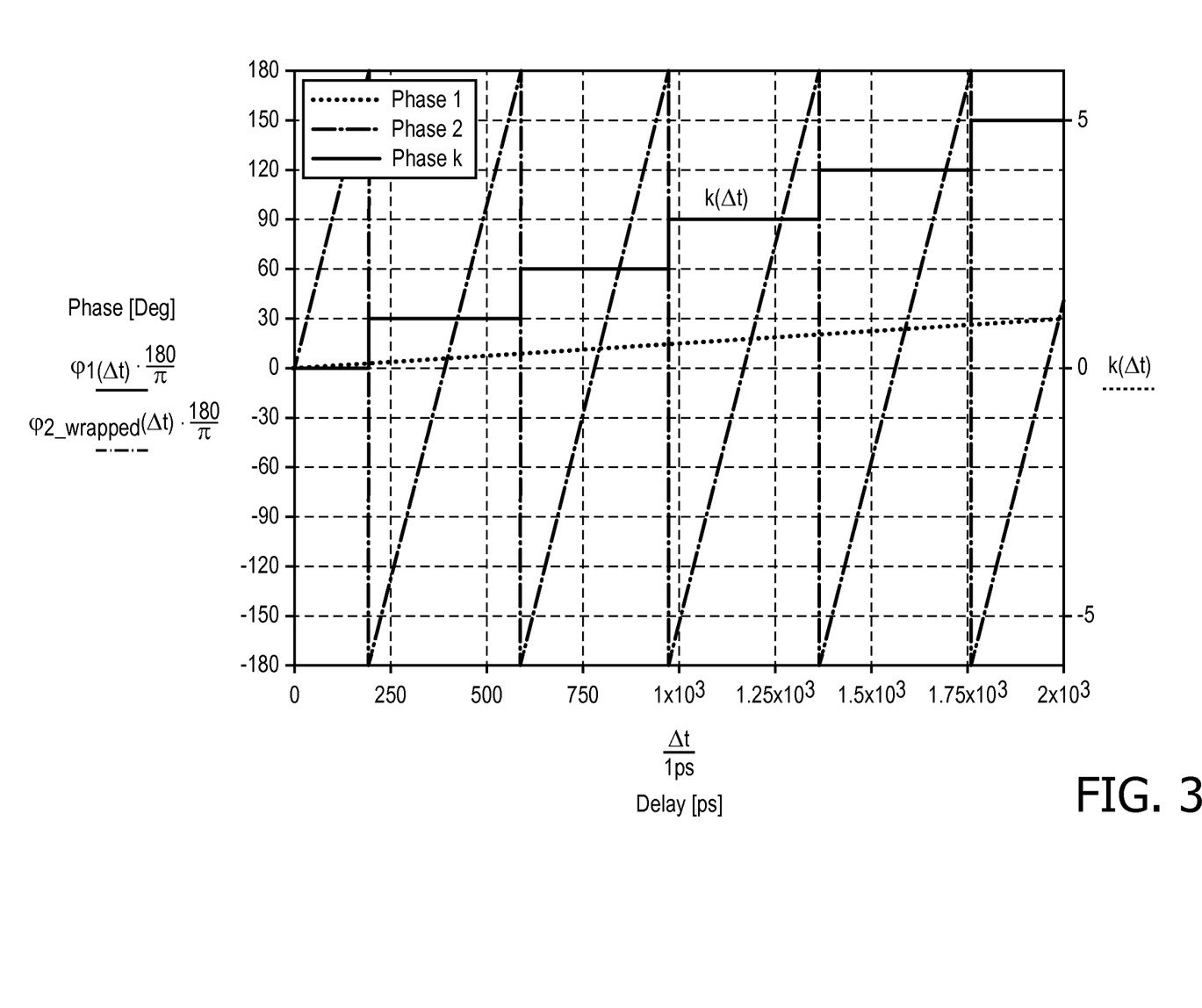
FIGS. 3 and 4 plot simulation results as described herein.
Figure 4:
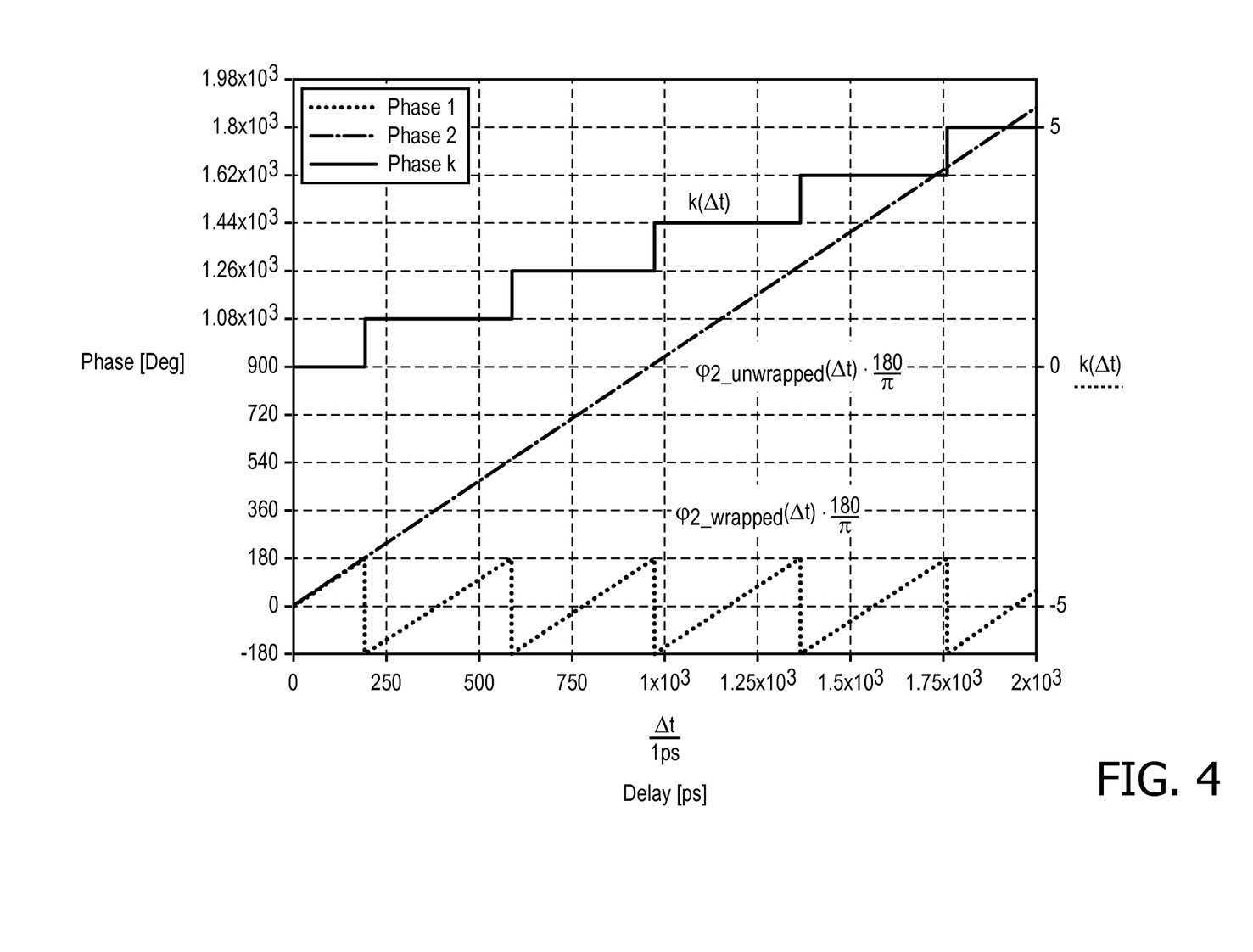

With reference to FIGS. 3 and 4, simulation results are presented using a Mathcad implementation of Equation (8). In the simulation: $N_1=1$; $N_2=128$; and $f_0=20$ MHz. FIG. 3 shows input data for a linear sweep of $\Delta t$ from 0 ps to 2000 ps. Shown are $\varphi_1$ and $\varphi_{2,wrapped}$ together with the values for k over the given range. As can be seen, $\varphi_1$ changes by only 30°, while $\varphi_{2,wrapped}$ gets wrapped 5 times from +180° to −180°. FIG. 4 shows the recovered carrier phase $\varphi_{2,unwrapped}$ along with the k value and the measured carrier phase $\varphi_{2,wrapped}$.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A clocked electronic device comprising:
a wireless receiver or transceiver configured to receive a propagation-delayed wireless clock synchronization signal comprising first and second propagation-delayed carrier signals at respective first and second carrier frequencies separated by a frequency difference;
a clock comprising a local oscillator driving a digital counter; and
at least one electronic signal processing component configured to perform clock synchronization including:
determining a wrap count (k) from a phase difference ($\varphi_1$) between phases of the first and second propagation-delayed carrier signals;
unwrapping a wrapped phase ($\varphi_{2,wrapped}$) of the propagation-delayed wireless clock synchronization signal using the wrap count to generate an unwrapped phase ($\varphi_{2,unwrapped}$); and
synchronizing the clock using the unwrapped phase.

2. The clocked electronic device of claim 1, wherein the clock synchronization further includes:
determining a propagation delay ($\Delta t$) of the propagation-delayed wireless clock synchronization signal from the unwrapped phase ($\varphi_{2,unwrapped}$); and
synchronizing the clock using the determined propagation delay.

3. The clocked electronic device of claim 1, wherein the clocked electronic device comprises a wireless medical imaging device component configured to collect samples of physiological or medical imaging data and the at least one electronic signal processing component is further configured to assign timestamps to the samples wherein the timestamps are obtained from the clock synchronized using the unwrapped phase.

4. The clocked electronic device of claim 3, wherein the wireless medical imaging device component comprises a wireless magnetic resonance (MR) receive coil configured for use with an MR imaging device.

5. The clocked electronic device of claim 4, wherein the first carrier frequency is equal to or greater than 1 GHz, the second carrier frequency is equal to or greater than 1 GHz, and the frequency difference between the first and second carrier frequencies is less than or equal to 100 MHz.

6. The clocked electronic device of claim 1, wherein the wrapped phase ($\varphi_{2,wrapped}$) of the propagation-delayed wireless clock synchronization signal is the wrapped phase of one of:
the first propagation-delayed carrier signal,
the second propagation-delayed carrier signal,
a combined signal that combines the first and second propagation-delayed carrier signals, and
a third propagation-delayed carrier signal of the propagation-delayed wireless clock synchronization signal wherein the third propagation-delayed carrier signal is different from the first propagation-delayed carrier signal and is different from the second propagation-delayed carrier signal.

7. The clocked electronic device of claim 1 further comprising:
a wireless clock synchronization signal generator including:
a radio frequency (RF) signal generator configured to generate a clock synchronization signal; and
a transmitter or transceiver connected to wirelessly transmit the clock synchronization signal into free space as a wireless clock synchronization signal wherein the propagation-delayed wireless clock synchronization signal comprises the wireless clock synchronization signal transmitted through free space to the wireless receiver or transceiver.

8. The clocked electronic device of claim 7, wherein the RF signal generator comprises a dual sideband (DSB) modulator configured to modulate a master carrier signal with a baseband signal at a baseband frequency equal to one-half of the frequency difference between the first and second carrier frequencies.

9. The clocked electronic device of claim 7 wherein,
the wireless receiver or transceiver, the clock, and the at least one electronic signal processing component comprise a wireless device; and
the wireless clock synchronization signal generator is not part of the wireless device.

10. A magnetic resonance (MR) receive coil comprising:
at least one coil element configured to receive an MR signal;
a wireless receiver or transceiver configured to receive a propagation-delayed wireless clock synchronization signal comprising first and second propagation-delayed carrier signals at respective first and second carrier frequencies separated by a frequency difference;
an on-board clock; and
at least one electronic signal processing component configured to generate timestamped samples of the MR signal received by the at least one coil element using the on-board clock and further configured to perform clock synchronization including:
determining a wrap count (k) from a phase difference ($\varphi_1$) between phases of the first and second propagation-delayed carrier signals;
unwrapping a wrapped phase ($\varphi_{2,wrapped}$) of the propagation-delayed wireless clock synchronization signal using the wrap count to generate an unwrapped phase ($\varphi_{2,unwrapped}$); and
synchronizing the on-board clock of the MR receive coil using the unwrapped phase.

11. The MR receive coil of claim 10 wherein the clock synchronization further includes:
determining a propagation delay ($\Delta t$) of the propagation-delayed wireless clock synchronization signal from the unwrapped phase ($\varphi_{2,unwrapped}$); and
synchronizing the on-board clock of the MR receive coil (20) using the determined propagation delay.

12. The MR receive coil of claim 10 wherein the at least one electronic signal processing component includes:
a preamplifier connected to amplify the MR signal received by the at least one coil element;
an analog-to-digital (A/D) converter connected to generate digital samples of the MR signal received by the at least one coil element and amplified by the preamplifier; and
an electronic processor including one or more of a digital microprocessor, a digital microcontroller, and a field-programmable gate array (FPGA) configured to assign timestamps to the digital samples using the on-board clock.

13. The MR receive coil of claim 10 wherein the on-board clock comprises a local oscillator driving a digital counter connected to the at least one electronic signal processing component.

14. The MR receive coil of claim 10 wherein the first carrier frequency is equal to or greater than 1 GHz, the second carrier frequency is equal to or greater than 1 GHz, and the frequency difference between the first and second carrier frequencies is less than or equal to 100 MHz.

15. The MR receive coil of claim 10 wherein one of:
the wireless receiver or transceiver is a wireless transceiver further configured to transmit the timestamped samples of the MR signal received by the at least one coil element off the MR receive coil; or
the MR receive coil further includes a wireless data output transmitter or transceiver separate from the wireless receiver or transceiver configured to receive a propagation-delayed wireless clock synchronization signal wherein the wireless data output transmitter or transceiver is configured to transmit the timestamped samples of the MR signal received by the at least one coil element off the MR receive coil.

16. A magnetic resonance (MR) imaging device comprising:
an MR imaging scanner;
the MR receive coil of claim 10; and
a wireless clock synchronization signal generator configured to transmit a wireless clock synchronization signal into free space wherein the propagation-delayed wireless clock synchronization signal comprises the wireless clock synchronization signal transmitted through free space to the wireless receiver or transceiver of the MR receive coil.

17. The MR imaging device of claim 16 wherein the wireless clock synchronization signal generator comprises a dual sideband (DSB) modulator configured to modulate a master carrier signal with a baseband signal at a baseband frequency equal to one-half of the frequency difference between the first and second carrier frequencies.

18. A clock synchronization method comprising:
using a wireless receiver or transceiver, receiving a free space transmission of a propagation-delayed wireless clock synchronization signal comprising first and second propagation-delayed carrier signals at respective first and second carrier frequencies separated by a frequency difference; and
using at least one electronic signal processing component, performing operations including:
determining a wrap count (k) from a phase difference ($\varphi_1$) between phases of the first and second propagation-delayed carrier signals;
unwrapping a wrapped phase ($\varphi_{2,wrapped}$) of the propagation-delayed wireless clock synchronization signal using the wrap count to generate an unwrapped phase ($\varphi_{2,unwrapped}$); and
synchronizing an electronic clock using the unwrapped phase.

19. The clock synchronization method of claim 18 wherein:
the operations performed using the at least one electronic signal processing component further include determining a propagation delay ($\Delta t$) of the propagation-delayed wireless clock synchronization signal from the unwrapped phase ($\varphi_{2,unwrapped}$); and
the electronic clock is synchronized using the determined propagation delay.

20. The clock synchronization method of claim 18 wherein the wrapped phase ($\varphi_{2,wrapped}$) of the propagation-delayed wireless clock synchronization signal is the wrapped phase of one of:
the first propagation-delayed carrier signal,
the second propagation-delayed carrier signal,
a combined signal that combines the first and second propagation-delayed carrier signals, and
a third propagation-delayed carrier signal of the propagation-delayed wireless clock synchronization signal wherein the third propagation-delayed carrier signal is different from the first propagation-delayed carrier signal and is different from the second propagation-delayed carrier signal.

21. The clock synchronization method of claim 18 further comprising:
operating a radio frequency (RF) signal generator to generate a clock synchronization signal; and
wirelessly transmitting the clock synchronization signal into free space as a wireless clock synchronization signal wherein the propagation-delayed wireless clock synchronization signal comprises the wireless clock synchronization signal transmitted through free space to the wireless receiver or transceiver.

22. The clock synchronization method of claim 21 wherein the operating of the RF signal generator comprises:
operating the RF signal generator comprising a dual sideband (DSB) modulator to generate the clock synchronization signal by modulating a master carrier signal with a baseband signal at a baseband frequency equal to one-half of the frequency difference between the first and second carrier frequencies.

* * * * *